United States Patent
Nakamura et al.

(10) Patent No.: US 6,818,414 B1
(45) Date of Patent: Nov. 16, 2004

(54) METHOD OF PRETREATMENT OF SAMPLE FOR QUANTITATING CHOLESTEROL AND METHOD FOR QUANTITATING CHOLESTEROL IN SPECIFIC LIPOPROTEINS BY USING THE SAME

(75) Inventors: Mitsuhiro Nakamura, Ryugasaki (JP); Yuriko Taniguchi, Ryugasaki (JP); Mitsuhisa Manabe, Ryugasaki (JP); Mitsuaki Yamamoto, Ryugasaki (JP)

(73) Assignee: Daiichi Pure Chemicals Co., Ltd., Tokyo (JP)

(*) Notice: Subject to any disclaimer, the term of this patent is extended or adjusted under 35 U.S.C. 154(b) by 0 days.

(21) Appl. No.: 09/926,818
(22) PCT Filed: Jun. 14, 2000
(86) PCT No.: PCT/JP00/03860
§ 371 (c)(1),
(2), (4) Date: Dec. 21, 2001
(87) PCT Pub. No.: WO00/78999
PCT Pub. Date: Dec. 28, 2000

(30) Foreign Application Priority Data

Jun. 21, 1999 (JP) .......................................... 11/174624
Feb. 3, 2000 (JP) ..................................... 2000-026737

(51) Int. Cl.[7] .............................................. C12Q 1/60
(52) U.S. Cl. ....................................................... 435/11
(58) Field of Search .......................................... 435/11

(56) References Cited

U.S. PATENT DOCUMENTS

| | | | |
|---|---|---|---|
| 4,366,249 A | 12/1982 | Thum et al. | |
| 5,773,304 A | 6/1998 | Hino et al. | |
| 5,856,156 A | 1/1999 | Ambrosius et al. | |
| 6,057,118 A | 5/2000 | Nakamura et al. | |
| 6,333,166 B1 | 12/2001 | Nakamura et al. | |
| 6,479,249 B2 | 11/2002 | Matsui et al. | |
| 2002/0001819 A1 | 1/2002 | Matsui et al. | |
| 2002/0192732 A1 | 12/2002 | Matsui et al. | |

FOREIGN PATENT DOCUMENTS

| | | | |
|---|---|---|---|
| CA | 2 301 873 | 3/1999 | |
| EP | 676 642 | 10/1995 | |
| EP | 0 887 422 | 12/1998 | |
| EP | 0 887 422 A1 | 12/1998 | |
| EP | 0 913 484 A1 | 5/1999 | |
| FR | 2 877 766 | 12/1992 | |
| JP | 7-280812 | 10/1995 | |
| JP | 9-299 | 1/1997 | |
| JP | 10-14596 | 1/1998 | |
| JP | 11-155595 | * 6/1999 | |
| WO | WO 98/26090 | 6/1998 | |
| WO | WO 98/59068 A1 | * 12/1998 | ............ C12Q/1/60 |
| WO | WO 99/10526 | 3/1999 | |

OTHER PUBLICATIONS

Mendez, A.J. "Monesin and Brefeldin A Inhibit High Density Lipoprotein–meidated Cholesterol Efflux from Cholesterol–enriched Cells" Journal of Biological Chemistry, 1995, vol. 270 No. 11, pp. 5891–5900.*

Mendez, A. J., "Monensin and Brefeldin A Inhibit High Density Lipoprotein–Mediated Cholesterol Efflux from Cholesterol–Enriched Cells—Implications for Intracellular Cholesterol Transport", Journal of Biological Chemistry, American Society of Biological Chemists, Baltimore, MD, vol. 270, No. 11, Mar. 17, 1996, pp. 5891–5900.

Armand J. Mendez: "Monensin and Brefeldin A Inhibit High Density Lipoprotein–mediated Cholesterol Efflux from Cholesterol–enriched Cells" Journal of Biological Chemistry, vol. 270, No. 11, pp. 5891–5900 1995.

O. Al Rayyes, et al., Eur. J. Pharmacol., vol. 372, No. 3, 311–18 Enhancement of Low Density Lipoprotein Catabolism by Non–Steroidal Anti–Inflammatory Drugs in Cultured HepG2 Cells, May 21, 1999 Abstract only.

A. Endo, et al., Adv. Enzyme Regul., vol. 28: 53–64, "Biochemical Aspect of HMG CoA Reductase Inhibitors", 1989 Abstract only.

* cited by examiner

Primary Examiner—Sandra Saucier
(74) Attorney, Agent, or Firm—Oblon, Spivak, McClelland, Maier & Neustadt, P.C.

(57) ABSTRACT

A method of a pretreatment of a sample for quantitating cholesterol characterized by, before measuring cholesterol contained in specific lipoproteins, treating the sample containing lipoproteins with an enzyme, the substrate of which is free cholesterol, optionally together with a reaction accelerator; a method for quantitating cholesterol in specific lipoproteins by using the above method; and a kit for quantitating cholesterol in specific lipoproteins to be used in the above quantification method. By using this quantification method, cholesterol in a specific fraction can be conveniently, accurately and efficiently quantitated fundamentally without resort to polyanion, etc. Thus, this method is appropriately usable in various automatic analyzers.

8 Claims, 3 Drawing Sheets

[FIG. 1]
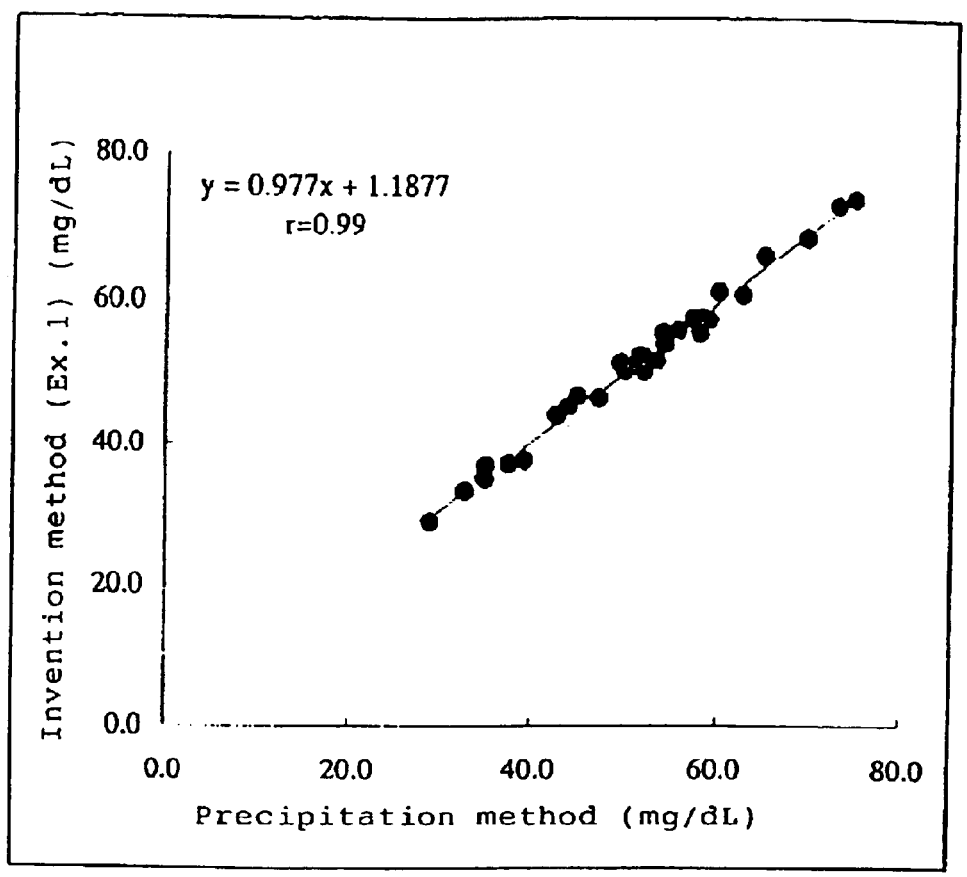

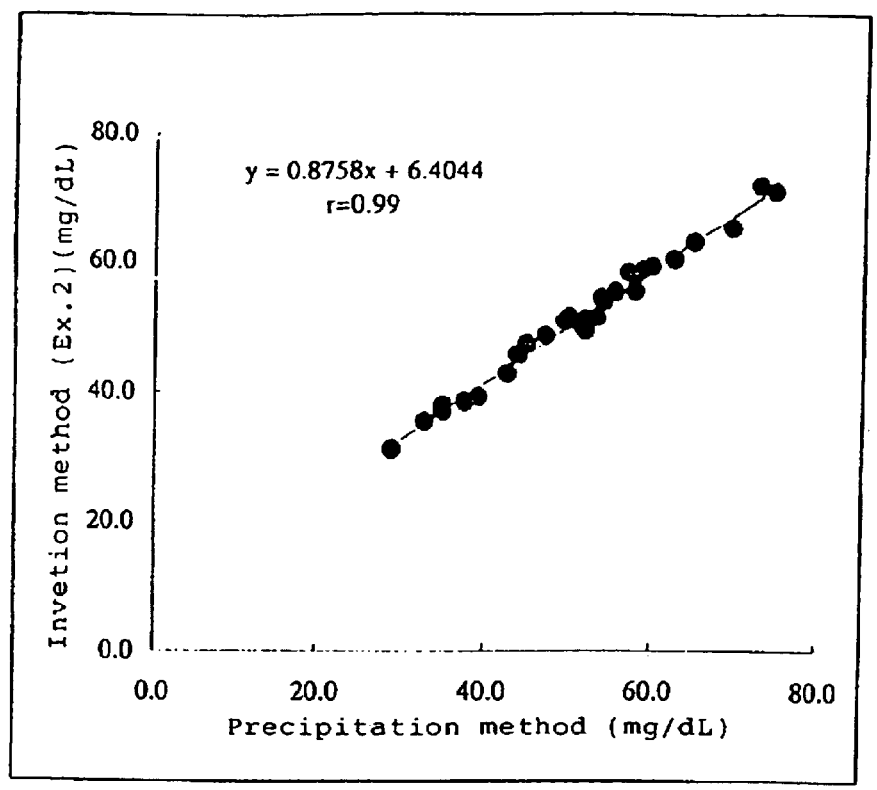
[FIG. 2]

[FIG. 3]
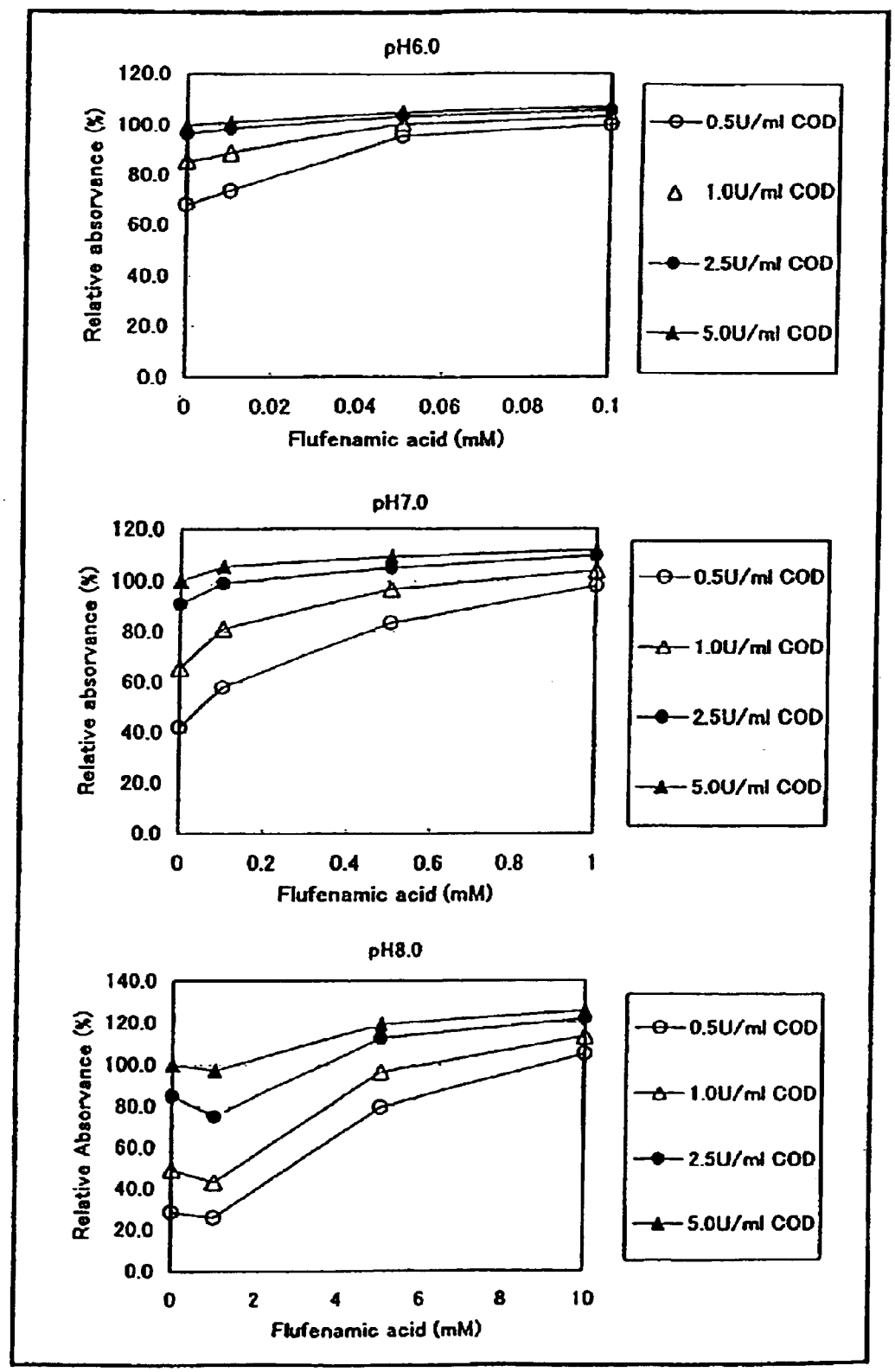

METHOD OF PRETREATMENT OF SAMPLE FOR QUANTITATING CHOLESTEROL AND METHOD FOR QUANTITATING CHOLESTEROL IN SPECIFIC LIPOPROTEINS BY USING THE SAME

TECHNICAL FIELD

This invention relates to a pretreatment method for accurately and efficiently discriminating and quantitating cholesterol, which exists in the specific lipoprotein fraction, by simple procedures while using a small amount of a sample, and also to a method for measuring cholesterol in the specific lipoprotein fraction by using the pretreatment method.

BACKGROUND ART

Lipids such as cholesterol are complexed with apoproteins in blood to form lipoproteins. Depending on differences in physical properties, lipoproteins are classified into chylomicron, very low density lipoprotein (VLDL), low density lipoprotein (LDL), high density lipoprotein (HDL), and so on. Among these lipoproteins, LDL is known to be one of causative substances which induce arteriosclerosis, while HDL is known to show anti-arteriosclerotic activity.

Epidemiologically, the level of cholesterol in LDL is known to exhibit a positive correlation with the frequency of onset of arteriosclerotic disease while the level of cholesterol in HDL is known to show an inverse correlation with the frequency of onset of arteriosclerotic disease. These days, measurements of cholesterol in LDL or HDL are, therefore, widely conducted for the prevention or diagnosis of ischemic heart diseases.

As methods known for the measurement of cholesterol in LDL or HDL, there are, for example, a method in which LDL or HDL is separated from other lipoproteins by ultracentrifugal separation and is then subjected to a cholesterol measurement; and another method in which subsequent to separation of LDL or HDL from other lipoproteins by electrophoresis, its lipid is stained, and the intensity of a developed color is measured. These methods are however not used practically, because they involve one or more problems in that procedures are intricate and many samples cannot be handled.

A method for the measurement of cholesterol in HDL, which is used at present in the field of clinical tests, is the precipitation method in which a precipitation reagent is added to a sample to agglutinate lipoproteins other than HDL, the resulting agglutinate is removed by centrifugation, and cholesterol in isolated supernatant which contains only HDL is then measured. This method is simpler compared with ultracentrifugation or electrophoresis, but due to the inclusion of the procedures to add the precipitation reagent and to perform the separation, requires each sample is a relatively large quantity, and involves a potential problem of causing an analytical error. Furthermore, the entire analysis steps of this method can not be fully automated.

On the other hand, enzymatic methods have been studied for the fractional quantitation of cholesterol in HDL. Known methods include, for example, to conduct an enzymatic reaction in the presence of a bile acid salt and a nonionic surfactant (JP 63-126498 A). This method makes use of the fact that an enzymatic reaction proceeds in proportion to the concentration of cholesterol in LDL in an initial stage of the reaction and the subsequent reaction velocity is in proportion to the concentration of cholesterol in HDL. A problem however exists in accuracy because the reaction with the cholesterol in HDL and the reaction with cholesterol in other lipoproteins cannot be fully distinguished.

Also included in the known methods is to have lipoproteins other than HDL agglutinated in advance, to cause cholesterol in HDL alone to react enzymatically, and to inactivate the enzyme and at the same time, to redissolve the agglutinate, followed by the measurement of an absorbance (JP 6-242110 A). This method, however, requires at least three procedures to add reagents so that it can be applied only to particular automated analyzers, leading to a problem in a wide applicability. Further, this method is not satisfactory from the standpoint of damages to analytical equipment and disposal of the reagents because of the use of a salt at a high concentration upon redissolution of an agglutinate.

A still further method is also known (JP 9-299 A), which comprises causing, in a first reaction, cholesterol oxidase and cholesterol esterase to act upon lipoproteins other than HDL in the presence of a special surfactant and to have cholesterol, which is contained in such other lipoproteins, preferentially reacted, and then measuring cholesterol in HDL while inhibiting any reaction to cholesterol in lipoproteins other than HDL. This method, however, is considerably different from the present invention inter alia in that in the first reaction, the special surfactant, cholesterol oxidase and cholesterol esterase are required at the same time to put, outside the reaction system, both free cholesterol and esterified cholesterol in the lipoproteins other than HDL.

Further, Japanese Patent No.2,600,065 discloses a method which makes combined use of a precipitation reagent, which is adapted to cause precipitation of lipoproteins other than HDL, and a cholesterol measuring reagent to measure cholesterol (HDL-C) in unprecipitated HDL. This method has practical utility when a modified enzyme is used as enzyme and α-cyclodextrin sulfate is used as a precipitation reagent. This method, however, also involves a problem in accuracy in that turbidity, which occurs as a result of the use of the precipitation reagent, interferes with the measurement system.

Concerning the measurement of HDL-C by a modified enzyme, "SEIBUTSU SHIRYO BUNSEKI (ANALYSIS OF BIOLOGICAL SAMPLES)", 19(5), 305–320, which is considered to be a published paper on the above-described patented method, discloses that, under the recognition of incapability of measurement of HDL-C in a serum of a hyperlipidemic patient by the modified enzyme due to a positive error (that is, to result in a higher value compared with that obtained by the precipitation method) induced when the modified enzyme is simply introduced into a reaction system, HDL-C was measured by using cyclodextrin sulfate, a polyanion, and magnesium chloride as a precipitation reagent for the avoidance of the positive error.

To reduce the influence of turbidity caused by a precipitation reagent in the above-described patented method, certain techniques are also known, including to make a surfactant exist concurrently (JP 8-116996 A), to use an antibody (JP 9-96637 A), and to employ a sugar compound (JP 7-301636 A). They, however, all require as a premise the inclusion of a reagent which induces formation of an agglutinate, so that it is fundamentally indispensable for them to use a precipitation reagent such as a polyanion.

The present inventors recently found that use of a substance, which acts upon the specific lipoprotein only, makes it possible to accurately quantitate cholesterol in the specific lipoprotein fraction without using a precipitation reagent, and filed patent applications (JP 9-244821). This method has an extremely high correlation with the conventional precipitation method, but compared in measurement values with the precipitation method, this method is recognized to have a similar tendency as the above-described method reported in "SEIBUTSU SHIRYO BUNSEKI (ANALYSIS OF BIOLOGICAL SAMPLES)". To obtain data consistent with those obtained by the conventional precipitation method at medical institutions and the like, a polyanion or the like is added.

From the standpoint of the problem of a tarnish or the like on a cuvette and scattering of measurement values, however, it is not desired to add a polyanion or the like and to form a precipitate in a measurement system. Accordingly, it has been strongly desired to eliminate the precipitate from the system. Further, it is also economically unreasonable to use a polyanion or the like for making the resulting data consistent with those obtained by the precipitation method although the polyanion or the like is not needed from the standpoint of the principle of the measurement. Hence, there is also an outstanding desire for its solution.

An object of the present invention is, therefore, to provide a method, which can accurately and efficiently quantitate cholesterol in the specific lipoprotein fraction by simple procedures fundamentally without needing a polyanion or the like and is suitably applicable to various automated analyzers.

DISCLOSURE OF THE INVENTION

The present inventors proceeded with a thorough investigation for a cause which may be responsible for the above-described problem reported in "SEIBUTSU SHIRYO BUNSEKI (ANALYSIS OF BIOLOGICAL SAMPLES)", that is, the problem that a value of cholesterol in the specific lipoprotein fraction as quantitated by using a substance which acts only upon a specific lipoprotein such as HDL becomes higher than the corresponding value as determined by the precipitation method; and came to a conclusion that even from non-HDL lipoproteins (LDL, VLDL and the like) the cholesterol of which is not supposed to be measured, a small amount of free cholesterol existing on their surfaces or in the vicinity of their surfaces is liberated to cause a positive error. Based on this finding, it has been found that a cholesterol value obtained by a quantitation method making use of a substance, which acts upon a specific lipoprotein only, becomes consistent with the corresponding value obtained by the precipitation method when the cholesterol value is measured after consuming only free cholesterol in advance under conditions that lipoproteins remain substantially unchanged, leading to the completion of the present invention.

Described specifically, the present invention provides a method for pretreating a sample, which contains various lipoproteins, prior to measuring cholesterol existing in specific one of the lipoproteins in the sample, which comprises causing an enzyme, which acts upon free cholesterol as a substrate, to act upon the sample to consume only the free cholesterol in advance under conditions that the lipoproteins remain substantially unchanged.

The present invention also provides a method for quantitating cholesterol existing in a specific lipoprotein in a sample, which comprises causing an enzyme, which acts upon free cholesterol as a substrate, to act upon the sample with the lipoprotein contained therein to consume only the free cholesterol under conditions that the lipoproteins remain substantially unchanged; and then measuring the cholesterol, which exists in the specific lipoprotein, by using a substance which acts upon the specific lipoprotein only.

BRIEF DESCRIPTION OF THE FIGURES

FIG. 1 is a diagram showing a correlation between the present invention in Example 1 and the precipitation method;

FIG. 2 is a diagram showing a correlation between the present invention in Example 2 and the precipitation method; and FIG. 3 is a diagram showing effects of a reaction accelerator in Example 5.

BEST MODES FOR CARRYING OUT THE INVENTION

In the present invention, before measuring cholesterol existing in a specific lipoprotein in a sample, an enzyme which acts upon free cholesterol as a substrate is caused to act, as pretreatment, upon the sample such that the free cholesterol is consumed.

As the enzyme which acts upon free cholesterol as a substrate, any enzyme can be used insofar as it acts upon free cholesterol as a substrate. Illustrative are cholesterol dehydrogenase and cholesterol oxidase. They can be of any origins such as microorganism origins, animal origins or plant origins, and can also be those prepared by genetic engineering. Further, they can be either modified or unmodified chemically. The enzyme is generally used at 0.001 to 100 U/mL, with 0.1 to 100 U/mL being preferred.

No particular limitation is imposed on conditions under which the above-described enzyme, which acts upon free cholesterol as a substrate, is caused to act upon the sample, and conditions recommended for the enzyme can be used. It is however necessary to pay attention so that, during a stage in which the enzyme which acts upon free cholesterol as a substate is caused to act upon the sample, a reaction through which an esterified cholesterol is converted into free cholesterol does not take place. Namely, it is not important whether or not cholesterol esterase exists. What is needed is to maintain conditions such that cholesterol esterase is not allowed to act practically.

Along with the enzyme which acts upon free cholesterol as a substrate, a coenzyme can be used as needed. As the coenzyme, nicotinamide adenine dinucleotide or the like is usable. Such coenzymes can be used either singly or in combination. The amount to be used varies depending on the coenzyme. The coenzyme may be used at 0.001 to 100 U/mL, preferably at 0.1 to 100 U/mL, although no particular limitation is imposed thereon.

Concerning the enzyme which acts upon free cholesterol as a substrate and is used in the present invention, no limitation is imposed on its origin as described above. Its concentration and the like can be chosen suitably to achieve desired performance and handling ease. Accordingly, if it is desired to have the pretreatment completed in a predetermined time, for example, it is only necessary to use the enzyme in a greater amount, and if it is conversely desired to save the enzyme, it is only necessary to make the pretreatment time longer.

In the case of a diagnostic reagent for exclusive use in measurements by automated analyzers, however, it is desired to meet both of the requirements at the same time. Namely, it is required to complete the pretreatment in a short time by using the enzyme in a small amount. In such a case, concurrent existence of a reaction accelerator selected from the below-described group in the pretreatment, which uses an enzyme which acts upon free cholesterol as a substrate, makes it possible to achieve desired performance with a reduced amount of the enzyme without making the pretreatment time longer.

Reaction accelerators usable for the above purpose can include, for example, flufenamic acid, mefenamic acid, 2,2',6',2''-terpyridine, tiglic acid, fusidic acid, betamethasone acetate, monensin and mevinolin, including their salts and metal derivatives (aluminum derivatives and the like) wherever such salts and metal derivatives exist. Among these, flufenamic acid and mefenamic acid are known as non-steroidal anti-inflammatory drugs, and fusidic acid and monensin are known as antibiotics.

Upon using such a compound as a reaction accelerator, it is necessary to suitably choose its concentration and the like by taking into consideration its physical properties, pH and ionic strength of the measurement system, and the kinds and concentrations of substances existing together.

The concentration of the reaction accelerator can be experimentally determined in accordance with conditions of a measuring system. In general, however, flufenamic acid can may be used at about 0.01 to 100 mM; fusidic acid at about 0.01 to 10 mM; mefenamic acid, 2,2',6',2''-terpyridine and betamethasone acetate, each, at about 0.01 to 5 mM; monensin and mevinolin, each, at about 0.01 to 1 mM; and tiglic acid at about 1 to 500 mM.

Use of the above-described reaction accelerator has made it possible to reduce the amount of the enzyme, which acts upon free cholesterol as a substrate, to one severalth or to one several tenth. When the enzyme is used in the same amount, on the other hand, the reaction accelerator can shorten the reaction time.

In the above-described pretreatment by the enzyme which acts upon free cholesterol as a substrate (and also by the reaction accelerator, if needed), it is also possible to use other enzymes (with exclusion of those giving substantial influence to lipoproteins) and salts, buffers for pH regulation, surfactants (with exclusion of those giving substantial influence to lipoproteins), preservatives, proteins such as albumin, and agents having affinity to specific lipoproteins, such as antibodies, antibiotics, saponins, lectins and polyanions to extents not causing agglutination of the specific lipoprotein, such that the action of the enzyme is adjusted without impairing the specificity of the measurement.

In the present invention, those containing the following ingredients can, therefore, be used as pretreatment agents for measuring cholesterol existing in specific lipoproteins in samples.

(Essential ingredients)
Enzymes which act upon free cholesterol as a substrate, for example, cholesterol dehydrogenase and cholesterol oxidase.
(Optional ingredients)
Reaction accelerators, for example, flufenamic acid, mefenamic acid, 2,2',6',2''-terpyridine, tiglic acid, fusidic acid, betamethasone acetate, monensin and mevinolin.
(Other ingredients)
coenzymes such as NAD, other enzymes such as peroxidase, catalase, diaphorase and ascorbate oxidase, acids such as pyruvic acid, salts, buffers for pH regulation, surfactants giving no substantial influence on lipoproteins, preservatives, proteins such as albumin, antibodies, antibiotics, saponins, lectins, polyanions and couplers such as 4-aminoantipyrine, oxidative color developers such as hydrogen donors, e.g., Trinder's reagent, electron acceptors such as phenazine methosulfate, and reductive color developers such as nitroblue tetrazolium.

In the present invention, cholesterol which exists in a specific lipoprotein in a sample is measured after having free cholesterol in lipoproteins consumed by the above-described pretreatment.

Any method can be used for the measurement of the cholesterol existing in the specific lipoprotein in the sample insofar as the method can measure the cholesterol existing in the specific lipoprotein by using a substance which acts upon the specific lipoprotein only.

An illustrative example of the method may comprise providing, as the substance which acts upon the specific lipoprotein, a surfactant selected from polyoxyethylene alkylene phenyl ethers or polyoxyethylene alkylene tribenzylphenyl ethers disclosed in JP 11-56395 A; adding a cholesterol measuring enzyme reagent in the presence of the substance; and then measuring the amount of cholesterol reacted in a time during which cholesterol in high density lipoprotein out of lipoproteins preferentially reacts with the cholesterol measuring enzyme reagent.

Examples of commercial products of the former surfactants, polyoxyethylene alkylene phenyl ethers, can include "Emulgen A-60" (trade name, product of Kao Corporation), while examples of commercial products of the latter surfactants, polyoxyethylene alkylene tribenzylphenyl ethers, can include "Emulgen B66" (trade name, product of Kao Corporation).

As an alternative method, there is a method which makes use of the modified enzymes, which are disclosed on pages 305–320 of "SEIBUTSU SHIRYO BUNSEKI (ANALYSIS OF BIOLOGICAL SAMPLES)", 19(5), as substances which act only upon specific lipoproteins, respectively. Although α-cyclodextrin sulfate and magnesium chloride are used in the method of this paper to inhibit reactions with lipoprotein fractions other than HDL, the use of the above-described pretreatment method of this invention makes it no longer necessary to use such substances.

Except for the use of the substance which acts upon the specific cholesterol, the method for the measurement of cholesterol existing in the specific lipoprotein can be practiced by using reagents employed in conventional cholesterol-measuring methods. Examples of ingredients which may be contained in reagents to be used can include enzymes such as cholesterol esterase, cholesterol oxidase, cholesterol dehydrogenase, isocitrate dehydrogenase, diaphorase and peroxidase, color developers, coenzymes, electron acceptors, proteins (albumin, etc.), preservatives, surfactants, salts, acids, and buffers for pH regulation.

As surfactants out of the above-described ingredients, both ionic and nonionic surfactants are usable. Illustrative are polyoxyethylene alkyl ethers, polyoxyethylene alkylphenyl ethers, polyoxyethylene-polyoxypropylene condensate, polyoxyethylene alkyl ether sulfates, alkylbenzenesulfonate salts, and bile acid salts. The amount of the surfactant to be used varies depending on the compound. The surfactant may however be used in 0.0001% to 5%, preferably in 0.001% to 5%, although no particular limitation is imposed thereon.

No particular limitation is imposed on the buffers. Conventional buffers such as Good's buffer, phosphate buffer, Tris buffer and phthalate buffer are usable. The buffer may be used at 0.005 M to 2 M, preferably 0.01 M to 1 M, although no particular limitation is imposed thereon.

The method for quantitating cholesterol in a specific lipoprotein fraction by the present invention typically comprises firstly adding a pretreatment agent, which acts upon free cholesterol only, into a measureing sample and causing the pretreatment agent to act upon the sample, and then adding and mixing a cholesterol measuring reagent (hereafter called a "quantitation reagent"), which contains a substance capable of acting upon the specific lipoprotein and a reagent employed for a conventional cholesterol-measuring method, to measure the amount of cholesterol in the specific lipoprotein fraction.

Specific examples can include, but are not limited to, a method which comprises mixing cholesterol dehydrogenase and a coenzyme (NAD) with a sample and then adding a cholesterol-measuring reagent which comprises cholesterol esterase and cholesterol oxidase; a method which comprises mixing cholesterol dehydrogenase and NAD with a sample and then adding a cholesterol-measuring reagent which comprises cholesterol esterase; a method which comprises mixing a sample and cholesterol oxidase together with peroxidase, 4-amino antipyrine or catalase and then adding a cholesterol-measuring reagent which comprises cholesterol esterase; and a method which comprises mixing a sample and cholesterol oxidase together with peroxidase, 4-aminoantipyrine, etc. and then adding a cholesterol-measuring reagent which comprises cholesterol esterase, cholesterol dehydrogenase and NAD.

Examples of the method for measuring cholesterol in a specific lipoprotein fraction can include a method making combined use of cholesterol esterase and cholesterol oxidase as an enzyme reagent and a method making combined use of cholesterol esterase and cholesterol dehydrogenase, although known enzyme assays are all usable.

In the present invention, the enzyme for use in the first reaction as the pretreatment reaction and the enzyme for use in the measurement of cholesterol as the quantitation method through the second reaction may be either the same or different. Further, the enzyme may be used in an excess amount in the first reaction and may also be used in the second reaction. In essence, it is only necessary to consume free cholesterol, which exists in a small amount on lipoprotein surfaces, (first reaction/pretreatment reaction) and then to bring the reaction system into a state, in which the enzyme acts only upon the specific lipoprotein to be measured, so that most cholesterol (free cholesterol+esterified cholesterol) forming the lipoprotein can be quantitated.

Further, no particular limitation is imposed on the method for finally detecting cholesterol after the addition of such a cholesterol-measuring enzyme reagent. It is possible to use, for example, absorptiometry in which detection is conducted by combining peroxidase with a chromogen or diaphorase or an electron acceptor with a reductive color-developing reagent; or a method in which a coenzyme or hydrogen peroxide is directly detected. The coenzyme may be amplified by a coenzyme cycling system.

To practice the method of the present invention with ease, it is preferred to use a quantitation kit which is suited for measuring cholesterol in the specific lipoprotein.

Although such kits can be readily designed based on the above explanation, their examples will be described next by dividing them into those making use of cholesterol oxidase and those making use of cholesterol dehydrogenase as typical example of enzymes which act upon free cholesterol as a substrate.

[Kits Making Use of Cholesterol Oxidase]
  (a) A quantitation kit for cholesterol in a specific lipoprotein, comprising the following reagents (1) and (2):
    (1) a first reagent comprising cholesterol oxidase and a hydrogen peroxide consuming substance (and further comprising a reaction accelerator in some instances); and
    (2) a second reagent comprising a substance which acts upon the specific lipoprotein only, cholesterol esterase, and a color developer.
  (b) A quantitation kit for cholesterol in a specific lipoprotein, comprising the following reagents (1) and (2):
    (1) a first reagent comprising cholesterol oxidase, cholesterol esterase, and a hydrogen peroxide consuming substance (and further comprising a reaction accelerator in some instances); and
    (2) a second reagent comprising a substance which acts upon the specific lipoprotein only, and a color developer.
  (c) A quantitation kit for cholesterol in a specific lipoprotein, comprising the following reagents (1), (2) and (3):
    (1) a first reagent comprising cholesterol oxidase and a hydrogen peroxide consuming substance (and further comprising a reaction accelerator in some instances);
    (2) a second reagent comprising a substance which acts upon the specific lipoprotein only; and
    (3) a third reagent comprising cholesterol esterase and a color developer.

In the above-described kits, the term "hydrogen peroxide consuming substance" means a substance which consumes and eliminates hydrogen peroxide produced by the reaction between cholesterol oxidase and cholesterol. Illustrative are catalase, couplers such as 4-aminoantipyrine, and oxidative-reductive color developer agents including hydrogen donors such as Trinder's reagent.

Among these, a coupler such as 4-aminoantipyrine and a hydrogen donor such as Trinder's reagent develop a color when reacted, in combination, with hydrogen peroxide, and are usable as the color developer in the above-described reagent (2) or (3). As the reagent (1) for use in the pretreatment step according to the present invention, it is preferred to use only one of a coupler and a hydrogen donor and to have hydrogen peroxide consumed through a non-color developing reaction. Needless to say, it is also possible to subject hydrogen peroxide to a color-developing reaction and then to make an adjustment to a measured value [this adjustment can be made by subtracting the intensity of a color, which is developed by the reagent (1), from the intensity of a color developed by the reagent (2) or the reagent (3)].

[Kits Making Use of Cholesterol Dehydrogenase]
  (d) A quantitation kit for cholesterol in a specific lipoprotein, comprising the following reagents (1) and (2):
    (1) a first reagent comprising cholesterol dehydrogenase and a coenzyme(and further comprising a reaction accelerator in some instances); and
    (2) a second reagent comprising a substance, which acts upon the specific lipoprotein only, and cholesterol esterase.
  (e) A quantitation kit for cholesterol in a specific lipoprotein, comprising the following reagents (1) and (2):
    (1) a first reagent comprising cholesterol dehydrogenase and a coenzyme(and further comprising a reaction accelerator in some instances); and
    (2) a second reagent comprising a substance which acts upon the specific lipoprotein only, cholesterol oxidase, cholesterol esterase, peroxidase, and a color developer.

(f) A quantitation kit for cholesterol in a specific lipoprotein, comprising the following reagents (1) and (2):
  (1) a first reagent comprising cholesterol dehydrogenase, a coenzyme, and cholesterol esterase (and further comprising a reaction accelerator in some instances); and
  (2) a second reagent comprising a substance which acts upon the specific lipoprotein only.

(g) A quantitation kit for cholesterol in a specific lipoprotein, comprising the following reagents (1) and (2):
  (1) a first reagent comprising cholesterol dehydrogenase, a coenzyme, and cholesterol esterase (and further comprising a reaction accelerator in some instances); and
  (2) a second reagent comprising a substance which acts upon the specific lipoprotein only, cholesterol oxidase, peroxidase, and a color developer.

(h) A quantitation kit for cholesterol in a specific lipoprotein, comprising the following reagents (1), (2) and (3):
  (1) a first reagent comprising cholesterol dehydrogenase and a coenzyme(and further comprising a reaction accelerator in some instances);
  (2) a second reagent comprising a substance which acts upon the specific lipoprotein only; and
  (3) a third reagent comprising cholesterol esterase.

(i) A quantitation kit for cholesterol in a specific lipoprotein, comprising the following reagents (1), (2) and (3):
  (1) a first reagent comprising cholesterol dehydrogenase and a coenzyme(and further comprising a reaction accelerator in some instances);
  (2) a second reagent comprising a substance which acts upon the specific lipoprotein only; and
  (3) a third reagent comprising cholesterol oxidase, cholesterol esterase, peroxidase, and a color developer.

(j) A quantitation kit for cholesterol in a specific lipoprotein, comprising the following reagents (1) and (2):
  (1) a first reagent comprising cholesterol dehydrogenase, a coenzyme, and a coenzyme reaction product consuming substance (and further comprising a reaction accelerator in some instances); and
  (2) a second reagent comprising a substance, which acts upon the specific lipoprotein only, and cholesterol esterase.

(k) A quantitation kit for cholesterol in a specific lipoprotein, comprising the following reagents (1) and (2):
  (1) a first reagent comprising cholesterol dehydrogenase, a coenzyme, and a coenzyme reaction product consuming substance(and further comprising a reaction accelerator in some instances); and
  (2) a second reagent comprising a substance which acts upon the specific lipoprotein only, cholesterol esterase, and a color developer.

In the above-described kits making use of cholesterol dehydrogenase, the term "coenzyme reaction product consuming substance" means a substance which converts a reduced coenzyme (for example, NADH), which occurs through the reaction among cholesterol, cholesterol dehydrogenase and a coenzyme (for example, NAD), back into the original coenzyme. Illustrative is a combination of lactate dehydrogenase and pyruvic acid (substrate). In each of the above-described kits, the reaction product of the coenzyme is produced by the addition of the reagent (1). In each of the kits (d), (f), (h) and (j) out of the above-described kits, light of the same wavelength as a color developed by the addition of the reagent (1) may be measured in the measurement stage without advance consumption of the reaction product. In this case, however, it is necessary to quantitate the cholesterol in the specific lipoprotein by subtracting the intensity of a color, which is developed in the pretreatment stage in which the reagent (1) is added, from the intensity of a color developed by the reagent (2) or the reagent (3). As an alternative, it may also be possible to add beforehand the substance, which consumes the reaction product, to the reagent (1) and subsequent to consumption of the reaction product, to add the reagent (2) or the reagent (3) for the development of a color. In this case, addition of a substance, which reduces the action of the substance which consumes the reaction product, to the reagent (2) or the reagent (3) is preferred. In each of the kits (e), (g), (I) and (k), on the other hand, it is not absolutely necessary to subtract the intensity of the color, which is developed in the pretreatment stage, from the color intensity measured in the measurement stage, because in the measurement stage, a developed color of a wavelength different from the color developed in the pretreatment stage is measured.

It is to be noted that the application of the above-mentioned reaction accelerators, such as flufenamic acid, mefenamic acid, 2,2',6',2"-terpyridine, tiglic acid, fusidic acid, betamethasone acetate, monensin and mevinolin, is limited neither to the pretreatment method or agent of the present invention nor the quantitation method or kit of the present invention for cholesterol in a specific lipoprotein, said quantitation method or kit making use of the pretreatment method or agent.

If a reaction accelerator such as fulfenamic acid is allowed to exist concurrently upon conducting a cholesterol quantitation method making use of an enzyme which acts upon free cholesterol as a substrate, for example, a free cholesterol quantitation method making combined use of cholesterol oxidase, peroxidase, a color developer and the like or a total cholesterol quantitation method making combined use of cholesterol oxidase, cholesterol esterase, peroxidase, a color developer and the like, it is obviously possible to bring about advantageous effects such that the amount of the enzyme to be used, said enzyme being capable of acting upon free cholesterol as a substrate and being cholesterol oxidase in the above-exemplified method, can be reduced and the time of the enzymatic reaction can be shortened.

Further, reference to the disclosure of this specification on the cholesterol quantitation method (for example, selection of a surfactant to limit a target of a specific lipoprotein to be measured) makes it possible to more specifically design a quantitation method as desired.

INDUSTRIALLY APPLICABILITY

The present invention has made it possible to efficiently quantitate cholesterol in a specific fraction by simple procedures without using a polyanion or the like, to say nothing of a mechanical pretreatment such as centrifugation. As the methods of the present invention do not form a precipitate which would otherwise occur by the addition of the polyanion or the like, measuring apparatus (especially, cuvettes) and the like remain free of a tarnish and moreover, measured values also remain free of scattering. The methods according to the present invention are, therefore, superior to the conventional cholesterol measuring methods.

Further, as will be demonstrated in subsequent Examples, measurement values showing a high correlation with those obtained by the conventional precipitation method can be obtained even with respect to samples with high triglyceride levels. Therefore, the methods according to the present invention are also excellent in that they are applicable to various samples without limitation.

In addition, the use of the reaction accelerator makes it possible to use the enzyme, which acts upon free cholesterol as a substrate, in a smaller amount in the pretreatment stage.

As has been described above, the methods according to the present invention permit accurate and specific measurements of a variety of samples by simple procedures while using the samples in small quantities. Accordingly, they can be applied to various automated analyzers and are also extremely useful in the field of clinical tests.

The present invention will next be described in further detail by the Examples. It should however be borne in mind that the present invention is by no means limited to the Examples.

EXAMPLE 1

With respect to each of 30 serum samples containing lipoproteins, the cholesterol in HDL was quantitated by the below-described method according to the present invention and the precipitation method, and the measurement values were compared.

(Invention Method)

10 mM phosphate buffer (First Reagent; pH 8.5) (300 μL), which contained 0.1 U/mL cholesterol dehydrogenase (product of Amano Pharmaceutical Co., Ltd.), 2.5 mM NAD and 0.03% 4-aminoantipyrine, was added to each sample (3 μL) (pretreatment). About 5 minutes later, a cholesterol quantitation reagent (Second Reagent) (100 μL)—which was composed of 100 mM MES buffer (pH6) containing 1% "Emulgen B-66", 1.3 U/mL cholesterol esterase (product of Asahi Chemical Industry Co., Ltd.), 2 U/mL cholesterol oxidase (product of Asahi Chemical Industry Co., Ltd.), 5 U/mL peroxidase (product of Toyobo Co., Ltd.) and 0.04% disulfobutylmetatoluidine—was added.

Just before the addition of the Second Reagent and upon an elapsed time of five minutes after the addition, the absorbance was measured at 600 nm. From a difference in absorbance, the concentration of HDL cholesterol in the serum sample was determined (2-point method). As a calibration substance, a control serum sample with a known concentration of HDL cholesterol was used. The above procedures were conducted using "Hitachi 7150 automated analyzer".

(Precipitation Method)

"HDLC 2 'Daiichi' Precipitant" (product of Daiichi Pure Chemicals Co., Ltd.) (200 μL) was mixed with the sample (200 μL), followed by centrifugation at 3,000 rpm for 10 minutes. The supernatant (50 μL) was collected, followed by the mixing with a cholesterol quantitation reagent (3 mL) composed of 100 mM MES buffer (pH6.5) containing 1% Triton X-100, 1 U/mL cholesterol esterase, 1 U/mL cholesterol oxidase, 5 U/mL peroxidase, 0.04% disulfobutylmetatoluidine and 0.04% 4-aminoantipyrine. After the resulting mixture was incubated at 37° C. for 10 minutes, its absorbance at 600 nm was measured to determine the concentration of the cholesterol in HDL.

(Results)

The results are shown in Table 1 and FIG. 1.

TABLE 1

| Sample No. | Precipitation method (mg/dL) | Invention method (mg/dL) |
| --- | --- | --- |
| 1 | 73 | 72 |
| 2 | 39 | 39 |
| 3 | 53 | 52 |
| 4 | 54 | 54 |
| 5 | 57 | 58 |
| 6 | 75 | 71 |
| 7 | 51 | 51 |
| 8 | 52 | 50 |
| 9 | 43 | 43 |
| 10 | 58 | 58 |
| 11 | 59 | 59 |
| 12 | 49 | 51 |
| 13 | 44 | 46 |
| 14 | 70 | 65 |
| 15 | 35 | 38 |
| 16 | 54 | 54 |
| 17 | 45 | 47 |
| 18 | 60 | 59 |
| 19 | 50 | 52 |
| 20 | 58 | 56 |
| 21 | 38 | 39 |
| 22 | 56 | 55 |
| 23 | 35 | 37 |
| 24 | 29 | 31 |
| 25 | 63 | 60 |
| 26 | 51 | 50 |
| 27 | 33 | 36 |
| 28 | 52 | 51 |
| 29 | 65 | 63 |
| 30 | 47 | 49 |

As is readily envisaged from the results, the invention method, despite the omission of a polyanion or the like, showed an extremely good correlation with the conventional precipitation method.

EXAMPLE 2

Measurements were conducted by another method of the present invention, which was similar to the invention method conducted in Example 1 except that in the first reagent, cholesterol dehydrogenase, NAD and the phosphate buffer were replaced by 5 U/mL cholesterol oxidase (product of Toyobo Co., Ltd.), 5 U/mL peroxidase (product of Toyobo Co., Ltd.) and 100 mM MES buffer (pH 6). The measurement values were compared with those obtained by the precipitation method in Example 1.

(Results)

The results are shown in Table 2 and FIG. 2.

TABLE 2

| Sample No. | Precipitation method (mg/dL) | Invention method (mg/dL) |
| --- | --- | --- |
| 1 | 73 | 73 |
| 2 | 39 | 38 |
| 3 | 53 | 52 |
| 4 | 54 | 56 |
| 5 | 57 | 57 |
| 6 | 75 | 74 |
| 7 | 51 | 52 |
| 8 | 52 | 50 |
| 9 | 43 | 44 |
| 10 | 58 | 58 |
| 11 | 59 | 57 |
| 12 | 49 | 51 |
| 13 | 44 | 45 |

TABLE 2-continued

| Sample No. | Precipitation method (mg/dL) | Invention method (mg/dL) |
|---|---|---|
| 14 | 70 | 69 |
| 15 | 35 | 37 |
| 16 | 54 | 54 |
| 17 | 45 | 47 |
| 18 | 60 | 61 |
| 19 | 50 | 50 |
| 20 | 58 | 55 |
| 21 | 38 | 37 |
| 22 | 56 | 56 |
| 23 | 35 | 35 |
| 24 | 29 | 29 |
| 25 | 63 | 61 |
| 26 | 51 | 52 |
| 27 | 33 | 33 |
| 28 | 52 | 52 |
| 29 | 65 | 66 |
| 30 | 47 | 46 |

As is readily envisaged from the results, the invention method, despite the omission of a polyanion or the like, showed an extremely good correlation with the conventional precipitation method.

EXAMPLE 3

Using the reagents of Example 1 and Example 2, five serum samples of different triglyceride levels were measured. The measurement values were then compared with those obtained by the precipitation method. The results are shown in Table 3.

TABLE 3

| | Precipitation method (mg/dL) | Invention method in Example 1 (mg/dL) | Invention method in Example 2 (mg/dL) | Triglyceride level (mg/dL) |
|---|---|---|---|---|
| Sample A | 47 | 49 | 49 | 198 |
| Sample B | 49 | 50 | 49 | 301 |
| Sample C | 26 | 27 | 24 | 742 |
| Sample D | 60 | 61 | 61 | 517 |
| Sample E | 37 | 40 | 36 | 428 |

As is shown in Table 3, measurement values of comparable levels with those obtained by the conventional method were also obtained by the present invention with respect to the samples of the high triglyceride levels.

EXAMPLE 4

Measurements were conducted in a similar manner as in Example 2 except that in the first reagent, 5 U/mL cholesterol oxidase was changed to give reagent compositions of the ingredient concentrations and combinations shown below in Table 4. The measurement values were compared with those obtained by the precipitation method and also with those obtained by the invention method (standard test system) of Example 2. Incidentally, as a second reagent, the same reagent as the second reagent employed in Example 1 was used. The results are shown in Table 5.

(Compositions of Testing Reagents)

TABLE 4

| Test system | Contents of composition |
|---|---|
| Standard | Cholesterol oxidase (5 U/mL) |
| A | Cholesterol oxidase (1 U/mL) |
| B | Flufenamic acid + cholesterol oxidase (0.15 mM)      (1 U/mL) |
| C | Mefenamic acid + cholesterol oxidase (0.1 mM)      (1 U/mL) |
| D | 2,2',6',2"-terpyridine + cholesterol oxidase (0.5 mM)      (1 U/mL) |
| E | Tiglic acid + cholesterol oxidase (50 mM)      (1 U/mL) |
| F | Fusidic acid + cholesterol oxidase (0.1 mM)      (1 U/mL) |
| G | Betamethasone acetate + cholesterol oxidase (0.2 mM)      (1 U/mL) |
| H | Monensin + cholesterol oxidase (0.2 mM)      (1 U/mL) |
| I | Mevinolin + cholesterol oxidase (0.05 mM)      (1 U/mL) |

(Results)

TABLE 5

| Sample | Precipitation method (mg/dL) | Test system (mg/dL) | | | | | | | | |
|---|---|---|---|---|---|---|---|---|---|---|
| | | Standard | A | B | C | D | E | F | G | H | I |
| 1 | 80 | 77 | 72 | 77 | 68 | 76 | 74 | 74 | 74 | 74 | 76 |
| 2 | 76 | 74 | 72 | 74 | 64 | 73 | 71 | 73 | 74 | 74 | 73 |
| 3 | 75 | 72 | 70 | 72 | 66 | 71 | 70 | 70 | 70 | 71 | 71 |
| 4 | 71 | 72 | 71 | 70 | 66 | 69 | 69 | 71 | 69 | 71 | 72 |
| 5 | 71 | 70 | 70 | 69 | 61 | 68 | 67 | 68 | 70 | 69 | 70 |
| 6 | 71 | 70 | 67 | 70 | 63 | 68 | 68 | 67 | 69 | 70 | 68 |
| 7 | 69 | 66 | 63 | 66 | 61 | 65 | 65 | 65 | 64 | 65 | 66 |
| 8 | 67 | 69 | 70 | 68 | 60 | 68 | 67 | 66 | 69 | 68 | 68 |
| 9 | 66 | 65 | 65 | 65 | 59 | 65 | 64 | 63 | 65 | 65 | 65 |
| 10 | 65 | 65 | 64 | 65 | 58 | 65 | 64 | 62 | 64 | 65 | 63 |
| 11 | 57 | 58 | 56 | 57 | 54 | 57 | 56 | 57 | 57 | 58 | 57 |
| 12 | 56 | 56 | 55 | 55 | 49 | 55 | 54 | 53 | 55 | 55 | 55 |
| 13 | 54 | 55 | 54 | 55 | 50 | 54 | 53 | 53 | 53 | 54 | 54 |
| 14 | 53 | 54 | 54 | 52 | 46 | 53 | 52 | 52 | 54 | 52 | 53 |
| 15 | 52 | 53 | 52 | 51 | 47 | 52 | 51 | 49 | 52 | 51 | 52 |

TABLE 5-continued

| Sample | Precipitation method (mg/dL) | Test system (mg/dL) | | | | | | | | |
|---|---|---|---|---|---|---|---|---|---|---|
| | | Standard | A | B | C | D | E | F | G | H | I |
| 16 | 51 | 53 | 51 | 50 | 46 | 50 | 51 | 49 | 51 | 51 | 51 |
| 17 | 49 | 50 | 48 | 48 | 44 | 47 | 48 | 47 | 48 | 48 | 49 |
| 18 | 47 | 48 | 48 | 46 | 41 | 46 | 46 | 45 | 47 | 47 | 47 |
| 19 | 45 | 46 | 48 | 44 | 38 | 46 | 43 | 45 | 47 | 47 | 46 |
| 20 | 47 | 47 | 49 | 45 | 40 | 46 | 45 | 45 | 48 | 47 | 47 |
| 21 | 42 | 44 | 44 | 43 | 39 | 43 | 42 | 41 | 43 | 44 | 43 |
| 22 | 39 | 42 | 43 | 41 | 37 | 41 | 41 | 39 | 41 | 41 | 41 |
| 23 | 32 | 35 | 36 | 33 | 31 | 36 | 34 | 32 | 34 | 34 | 33 |
| 24 | 18 | 20 | 22 | 19 | 17 | 23 | 19 | 18 | 21 | 20 | 19 |
| 25 | 40 | 42 | 42 | 41 | 38 | 45 | 41 | 40 | 41 | 42 | 41 |
| Correlation coef. | — | 0.996 | 0.990 | 0.998 | 0.992 | 0.995 | 0.997 | 0.997 | 0.994 | 0.995 | 0.997 |
| Slope | | 0.905 | 0.838 | 0.941 | 0.832 | 0.856 | 0.888 | 0.915 | 0.877 | 0.891 | 0.917 |
| Intercept | | 5.6 | 8.7 | 2.6 | 3.4 | 7.5 | 4.6 | 2.8 | 6.3 | 5.7 | 4.1 |

When the amount of cholesterol oxidase was reduced to one fifth (the test system A) compared with the standard test system (Example 2), the correlation coefficient slightly declined and the value of intercept slightly increased. When the reaction accelerator was used, however, results substantially comparable with those of the standard test system were obtained even when the amount of cholesterol oxidase was one fifth. It has hence become evident from these results that the use of a reaction accelerator makes it possible to reduce the amount of cholesterol oxidase to be used.

EXAMPLE 5

Reagents J to L shown below in Table 6 were prepared, which commonly contained 1.25 U/mL peroxidase (product of Toyobo Co., Ltd.), 0.01% 4-aminoantipyrine, 0.02% disulfo butyl-m-toluidine and 50 mM NaCl and were different from each other in the kind and pH of buffer and the concentrations of cholesterol oxidase (product of Toyobo Co., Ltd.) and fulfenamic acid (product of Sigma Chemical Co.).

TABLE 6

| Reagent | ① Buffer (pH)<br>② Concentration of cholesterol oxidase<br>③ Concentration of fulfenamic acid |
|---|---|
| J | ① 50 mM Bis-Tris (pH 6.0)<br>② 0.5, 1.0, 2.5, 5.0 U/mL<br>③ 0, 0.01, 0.05, 0.1 mM |
| K | ① 50 mM PIPES (pH 7.0)<br>② 0.5, 1.0, 2.5, 5.0 U/mL<br>③ 0, 0.1, 0.5, 1.0 mM |
| L | ① 50 mM MOPS (pH 8.0)<br>② 0.5, 1.0, 2.5, 5.0 U/mL<br>③ 0, 1.0, 5.0, 10.0 mM |

Reagents J to L (300 μL) were separately added to aliquots (3 μL) of each serum sample. After the resultant mixtures were incubated at 37° C. for 5 minutes, their absorbances were measured at 600 nm. The above procedures were conducted using the Hitachi 7150 automated analyzer.

Four serum samples were measured with Reagents J to L.

With respect to each of Reagents J to L, relative absorbances were calculated for the individual concentrations of cholesterol oxidase and fulfenamic acid by assuming that the absorbance obtained with a reagent containing 5.0 U/mL cholesterol oxidase and 0 mM fulfenamic acid was 100.

(Results)

Results, which had been obtained by averaging the relative absorbances of the four samples, are presented in FIG. 3. in which "COD" stands for cholesterol oxidase.

As is readily appreciated from the results, the relative absorbance increased depending upon the concentration of fulfenamic acid irrespective of the pH. It has, therefore, been confirmed that the use of the reaction accelerator makes it possible to reduce the amount of cholesterol oxidase to be used.

It has also become clear that the reaction accelerator is also usable in a method for the measurement of free cholesterol or total cholesterol, which makes use of an enzyme which acts upon free cholesterol as a substrate.

What is claimed is:

1. A method for pretreating a sample, which contains various lipoproteins, prior to measuring cholesterol existing in specific one of said lipoproteins in said sample, which comprises causing an enzyme, which acts upon free cholesterol as a substrate, and a reaction accelerator, which is selected from flufenamic acid, mefenamic acid, 2,2',6',2"-terpyridine, tiglic acid, fusidic acid, betamethasone acetate, monensin and mevinolin, to act upon said sample to convert only said free cholesterol in advance under conditions that said lipoproteins remain substantially unchanged.

2. A pretreatment method according to claim 1, wherein said enzyme is cholesterol oxidase or cholesterol dehydrogenase.

3. A method for quantitating cholesterol existing in a specific lipoprotein in a sample, which comprises causing cholesterol dehydrogenase, which acts upon free cholesterol as a substrate, to act upon said sample with said lipoprotein contained therein to convert only said free cholesterol under conditions that said lipoproteins remain substantially unchanged; and then measuring said cholesterol, which exists in said specific lipoprotein, by using a substance which acts upon said specific lipoprotein only.

4. A quantitation method according to claim 3, wherein said specific lipoprotein is high density lipoprotein.

5. A method for quantitating cholesterol existing in a specific lipoprotein in a sample, which comprises causing an enzyme, which acts upon free cholesterol as a substrate, and a reaction accelerator, which is selected from the flufenamic acid, mefenamic acid, 2,2',6',2"-terpyridine, tiglic acid, fusidic acid, betamethasone acetate, monensin and mevinolin, to act upon said sample with said lipoprotein contained therein to convert only said free cholesterol under conditions that said lipoproteins remain substantially unchanged; and then measuring said cholesterol, which exists in said specific lipoprotein, by using a substance which acts upon said specific lipoprotein only.

6. A quantitation method according to claim 5, wherein said enzyme is cholesterol oxidase and/or cholesterol dehydrogenase.

7. A quantitation method according to claim 5, wherein said specific lipoprotein is high density lipoprotein.

8. A method for quantitating free cholesterol in a sample which contains various lipoproteins, which comprises conducting a cholesterol oxidase reaction in said sample in the presence of a reaction accelerator selected from flufenamic acid, mefenamic acid, 2,2',6',2"-terpyridine, tiglic acid, fusidic acid, betamethasone acetate, monensin and mevinolin, and then measuring said free cholesterol.

* * * * *